(12) United States Patent
Anderson et al.

(10) Patent No.: US 6,264,968 B1
(45) Date of Patent: Jul. 24, 2001

(54) COMPOSITIONS AGAINST WOOD-DESTROYING INSECTS

(75) Inventors: John-Phillip-Evans Anderson, Langenfeld; Oliver Keuken, Köln, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/128,818

(22) Filed: Aug. 4, 1998

(30) Foreign Application Priority Data

Aug. 11, 1997 (DE) .............................. 197 34 665

(51) Int. Cl.⁷ .............................. A01N 43/40; A01N 25/00
(52) U.S. Cl. .............................. 424/405; 514/341
(58) Field of Search .............................. 424/405; 514/94, 514/226.8, 229.2, 245, 256, 341, 342, 343, 356, 365, 385, 449

(56) References Cited

U.S. PATENT DOCUMENTS

| 5,087,632 | | 2/1992 | Tsuboi et al. | 514/357 |
| 5,159,778 | * | 11/1992 | Metzner et al. | 43/121 |
| 5,712,295 | * | 1/1998 | Mencke et al. | 514/338 |
| 5,783,203 | * | 7/1998 | Shutte et al. | 424/405 |

FOREIGN PATENT DOCUMENTS

| 0 080 516 A1 | | 6/1983 | (EP) . |
| 0 250 751 | | 1/1988 | (EP) . |
| 250751 | * | 1/1988 | (EP) . |
| 0 279 207 A2 | | 8/1988 | (EP) . |
| 0 777 964 | * | 6/1997 | (EP) . |
| 05155709 | * | 6/1993 | (JP) . |
| 2031658 | * | 4/1995 | (RU) . |
| WO 95 14004 | | 11/1990 | (WO) . |
| WO 95/18532 | | 7/1995 | (WO) . |
| WO 97/17847 | | 5/1997 | (WO) . |
| WO 98 21960 | | 5/1998 | (WO) . |
| WO 98/19532 | | 5/1998 | (WO) . |

OTHER PUBLICATIONS

Derwent English Abstract of EP 0 250 751 A (2 pages).

* cited by examiner

Primary Examiner—Jose' G. Dees
Assistant Examiner—Alton Pryor
(74) Attorney, Agent, or Firm—Norris McLaughlin & Marcus

(57) ABSTRACT

The present invention relates to long-acting compositions against wood-destroying insects, characterized in that they contain
  a) insecticidally active compounds,
  b) organic natural compounds or organic synthetic compounds or mixtures thereof as carrier material,
  c) optionally microbicidally active compounds,
  d) optionally attractants or development-inhibitory compounds for insects,
  e) and optionally formulation auxiliaries.

3 Claims, No Drawings

COMPOSITIONS AGAINST WOOD-DESTROYING INSECTS

The present invention relates to long-acting compositions against wood-destroying insects, to their preparation and to their use.

It is known that the duration of action of crop protection agents can be extended by binding active compounds chemically to hydroxyl-group-containing wood derivatives such as sawdust, bark or lignin. However, to prepare the appropriate wood derivative/active compound complexes, complicated chemical reactions were required (Tappi/August 1971, Vol. 54, No. 8 p. 1293–1294; FR-P 1 544 406).

It is furthermore known that the action of insecticides can be extended by applying them to the soil shortly after a fertilization with organic fertilizers such as manure, compost, etc. (Archives of Environmental Contamination and Toxicology (1996) Vol. 31, No.1 p. 98–106).

Furthermore, it is known that UV-sensitive crop protection agents can be protected against UV-induced degradation by addition of lignin (WO 97/15 187).

Furthermore, it is known that polyoxyalkylene derivatives can be added as stabilizers to certain active compounds from the group of the nicotinoyl insecticides (EP-B 431 361).

Also known are baits against soil-dwelling insects, such as termites, which contain culture medium for fungi in addition to active compounds from the group of the nicotinoyl insecticides (ZA-P 94-7242).

For protecting wood-containing materials against destruction by insects, a long-term activity of the active compounds, in particular in the soil, is critical. Frequently, the duration of action of the insecticides employed is, owing to their degradation by soil-dwelling microorganisms, too short for protecting buildings.

The present invention relates to:
1. Compositions against wood-destroying insects, characterized in that they contain
   a) insecticidally active compounds,
   b) organic natural compounds or organic synthetic compounds or mixtures thereof as carrier material,
   c) optionally microbicidally active compounds,
   d) optionally attractants or development-inhibitory compounds for insects,
   e) and optionally formulation auxiliaries.
2. Method for delaying the microbial degradation of active compounds against wood-destroying insects in soil, characterized in that the active compounds are mixed with natural organic compounds or synthetic organic compounds, optionally with microbicidally active compounds, optionally with attractants or development-inhibitory compounds for insects and optionally formulation auxiliaries.
3. Compositions according to 1, characterized in that the insecticidally active compounds used are one or more active compounds from the group of the agonists or antagonists of the nicotinic acetylcholine receptors of insects.
4. Compositions according to 1, characterized in that the insecticidally active compound used is imidacloprid.
5. Compositions according to 1, characterized in that they are used in the soil for protecting buildings.
6. Compositions according to 1, characterized in that they are employed in the soil for protecting materials and buildings against termites.
7. Compositions according to 1, characterized in that they are packaged in water-soluble polymer films, paper films or paper tubes and employed in packaged form.
8. Compositions according to 7, characterized in that after packaging they are in the form of tubes, sausages, bags, pillows, mats, blocks, ropes or cylinders.
9. Compositions according to 1, characterized in that the carrier material has a particle size of up to 0.2 mm, that the compositions are suspended in water prior to use and applied to the soil or buildings as a suspension, or mixed with foaming agents and applied to the soil or buildings as a foam.
10. Compositions according to 1, characterized in that the carrier material has a particle size of 0.2 mm to 10 mm and is scattered onto the soil or incorporated into the soil.

The compositions according to the invention contain one or more agrochemical insecticidally active compounds.

The insecticides include agonists or antagonists of the nicotinic acetylcholine receptors of insects, phosphorus-containing compounds such as phosphoric or phosphonic esters, natural and synthetic pyrethroids, carbamates, amidines, juvenile hormones and juvenile hormone-like substances.

Agonists or antanogists of the nicotinic acetylcholine receptors of insects are known, for example, from European Patent Nos. 580 553, 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 30 455 000, 135 956, 471 372, 302 389; German Patent Nos. 3 639 877, 3 712 307; Japanese Patent Nos. 03 220 176, 02 207 083, 63 307 857, 63 287 764, 03 246 283, 04 9371, 03 279 359, 03 255 072; U.S. Pat. Nos. 5 034 524, 4 948 798, 4 918 086, 5 039 686, 5 034 404; PCT Applications No. WO 91/17 659, 91/4965; French Patent No. 2 611 114; Brazilian Application No. 88 03 621.

The compounds described in these publications and their preparation are expressly incorporated herein by way of reference.

These compounds are preferably represented by the general formula (A)

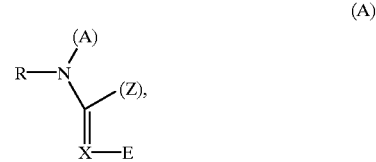

in which

R represents hydrogen, optionally substituted radicals from the group acyl, alkyl, aryl, aralkyl, heteroaryl or heteroarylalkyl;

A represents a monofunctional group from the series hydrogen, acyl, alky, aryl, or represents a bifunctional group which is linked to the radical Z;

E represents an electron-withdrawing radical;

X represents the radicals —CH= or =N—, it being possible for the radical —CH= instead of an H-atom to be linked to the radical Z;

Z represents a monofunctional group from the series alkyl, —O—R, —S—R,

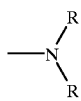

or represents a bifunctional group which is linked to the radical A or to the radical X (if X represents

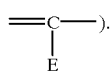

Particularly preferred compounds of the formula (A) are those in which the radicals have the following meaning:

R represents hydrogen and represents optionally substituted radicals from the series acyl, alkyl, aryl, aralkyl, heteroaryl, heteroarylalkyl.

Acyl radicals which may be mentioned are formyl, alkylcarbonyl, arylcarbonyl, alkylsulfonyl, arylsulfonyl, (alkyl)-(aryl)-phosphoryl, which may in turn be substituted.

As alkyl there may be mentioned $C_{1-10}$-alkyl, especially $C_{1-4}$-alkyl, specifically methyl, ethyl, i-propyl, sec- or t-butyl, which may in turn be substituted.

As aryl there may be mentioned phenyl, naphthyl, especially phenyl.

As aralkyl there may be mentioned phenylmethyl, phenethyl.

As heteroaryl there may be mentioned heteroaryl having up to 10 ring atoms and N, O, S especially N as heteroatoms. Specifically there may be mentioned thienyl, furyl, thiazolyl, imidazolyl, pyridyl, benzothiazolyl, As heteroarylalkyl there may be mentioned heteroarylmethyl, heteroarylethyl having up to 6 ring atoms and N, O, S, especially N as heteroatoms.

Substituents which may be listed by way of example and preference are: alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butylthio; halogenoalkyl having preferably 1 to 4, in particular 1 or 2 carbon atoms and preferably 1 to 5, in particular 1 to 3 halogen atoms, the halogen atoms being identical or different and being preferably fluorine, chlorine or bromine, especially fluorine, such as trifluoromethyl; hydroxyl; halogen, preferably fluorine, chlorine, bromine and iodine, especially fluorine, chlorine and bromine; cyano; nitro; amino; monoalkyl- and dialkylamino having preferably 1 to 4, in particular 1 or 2 carbon atoms per alkyl group, such as methylamino, methyl-ethylamino, n- and i-propylamino and methyl-n-butylamino; carboxyl; carbalkoxy having preferably 2 to 4, in particular 2 or 3 carbon atoms, such as carbomethoxy and carboethoxy; sulfo (—SO₃H); alkylsulfonyl having preferably 1 to 4, in particular 1 or 2 carbon atoms, such as methylsulfonyl and ethylsulfonyl; arylsulfonyl having preferably 6 or 10 aryl carbon atoms, such as phenylsulfonyl, and also heteroarylamino and heteroarylalkylamino such as chloropyridylamino and chloropyridylmethylamino.

A particularly preferably represents hydrogen and optionally substituted radicals from the series acyl, alkyl, aryl, which preferably have the meanings given for R. A additionally represents a bifunctional group. There may be mentioned optionally substituted alkylene having 1–4, in particular 1–2 C atoms, substituents which may be mentioned being the substituents listed earlier above, and it being possible for the alkylene groups to be interrupted by heteroatoms from the series N, O, S.

A and Z may, together with the atoms to which they are attached, form a saturated or unsaturated heterocyclic ring. The heterocyclic ring can contain a further 1 or 2 identical or different heteroatoms and/or hetero-groups. Heteroatoms are preferably oxygen, sulfur or nitrogen, and hetero-groups are preferably N-alkyl, where the alkyl in the N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are imidazolidine, pyrrolidine, piperidine, piperazine, hexamethyleneimine, hexahydro-1,3,5-triazine, hexahydrooxodiazine, morpholine, each of which may optionally be substituted preferably by methyl.

E represents an electron-withdrawing radical, in which context particular mention may be made of NO₂, CN, halogenoalkylcarbonyl such as 1,5-halogeno-$C_{1-4}$-carbonyl especially COCF₃.

X represents —CH= or —N=

Z represents optionally substituted radicals alkyl, —OR, —SR, —NRR, where R and the substituents preferably have the meaning given above.

Z can form, apart from the abovementioned ring, and together with the atom to which it is attached and with the radical

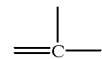

instead of X, a saturated or unsaturated heterocyclic ring. The heterocyclic ring can contain a further 1 or 2 identical or different heteroatoms and/or heterogroups. The heteroatoms are preferably oxygen, sulfur or nitrogen, and the hetero-groups N-alkyl, in which case the alkyl or N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are pyrrolidine, piperidine, piperazine, hexamethyleneimine, morpholine and N-methylpiperazine.

As compounds which may be used with very particular preference in accordance with the invention, mention may be made of compounds of the general formulae (II), (III) and (IV):

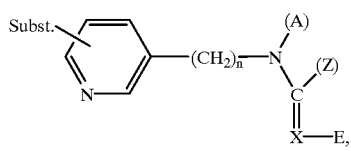 (II)
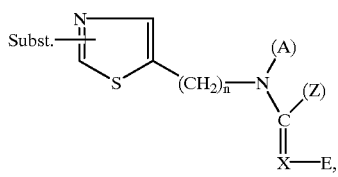 (III)
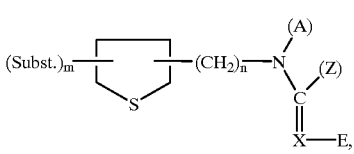 (IV)
in which
n represents 1 or 2,
m represents 0, 1 or 2,
Subst. represents one of the above-listed substituents, especially halogen, very particularly chlorine,
A, Z, X and E each have the meanings given above.
Specifically, the following compounds may be mentioned:
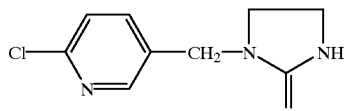
imidacloprid
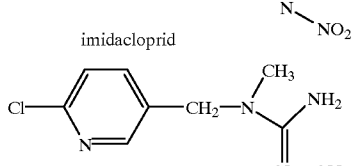
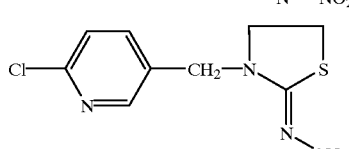
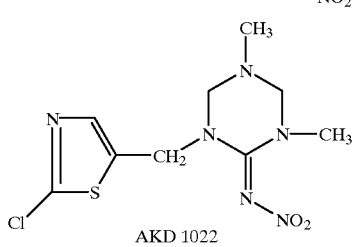
AKD 1022
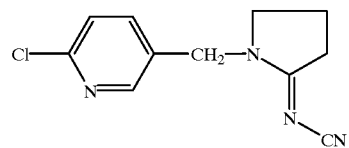
-continued
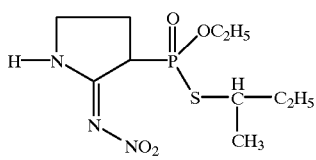
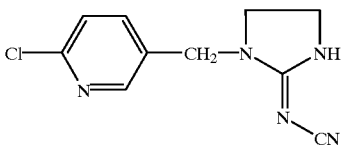
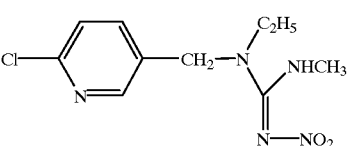
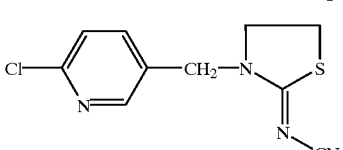
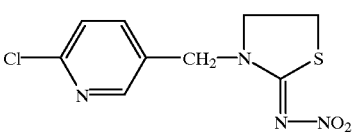
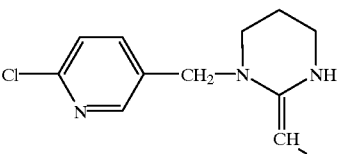
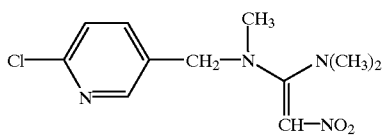
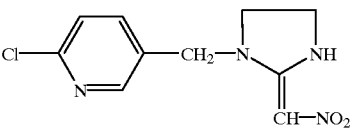
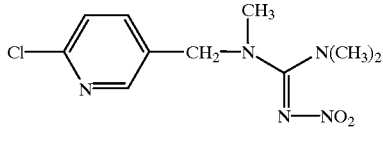
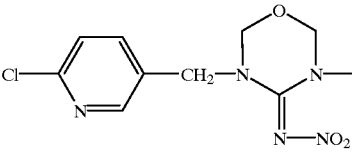
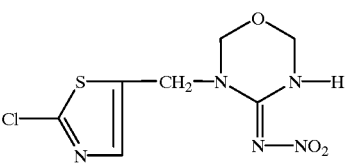

-continued
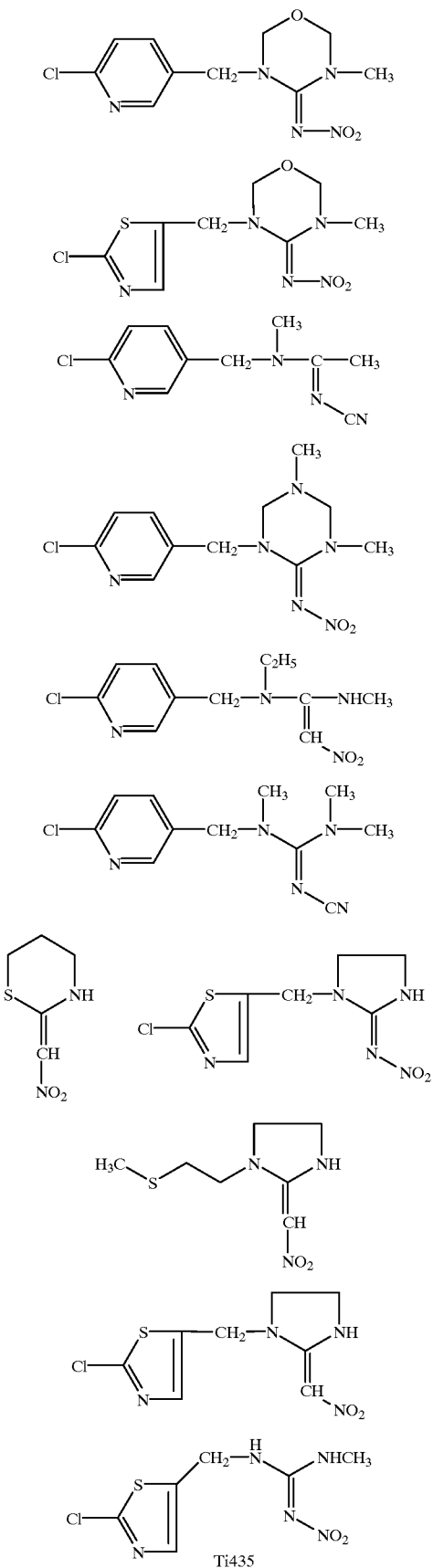
-continued
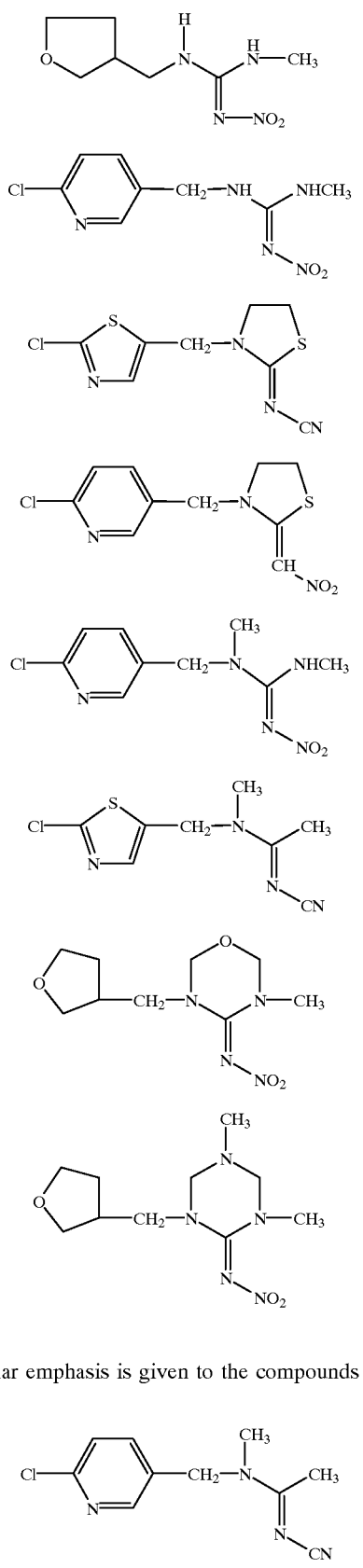
Particular emphasis is given to the compounds
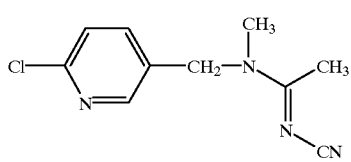

-continued

[chemical structure: 6-chloropyridin-3-yl-CH2-N(C2H5)-C(NHCH3)=CH-NO2]

[chemical structure: 2-chlorothiazol-5-yl-CH2-N-CH2-O-CH2-N(CH3)-C=N-NO2 (tetrahydrooxadiazine)]

[chemical structure: tetrahydrofuran-3-yl-CH2-NH-C(NHCH3)=N-NO2]

Furthermore, particular emphasis is given to the compounds

[chemical structure: 6-chloropyridin-3-yl-CH2-N(imidazolidine)=N-NO2, with NH]

[chemical structure: 6-chloropyridin-3-yl-CH2-N(thiazolidine)=N-CN]

[chemical structure: 2-chlorothiazol-5-yl-CH2-N-CH2-N(CH3)-C=N-NO2 with N-CH3 (triazinane)]

[chemical structure: 2-chlorothiazol-5-yl-CH2-NH-C(NHCH3)=N-NO2]

The phosphoric or phosphonic esters include:
O-Ethyl O-(8-quinolyl)phenyl thiophosphate (quintiofos),
O,O-Diethyl O-(3-chloro-4-methyl-7-coumarinyl) thiophosphate (coumaphos),
O,O-Diethyl O-phenylglyoxylonitrile-oxime thiophosphate (phoxim),
O,O-Diethyl O-cyanochlorobenzaldoxime thiophosphate (chlorphoxim),
O,O-Diethyl O-(4-bromo-2,5-dichlorophenyl) phosphorothioate (bromophos-ethyl),
O,O,O',O'-Tetraethyl S,S'-methylenebis (phosphorodithioate) (ethion),
2,3-p-dioxanedithiol S,S-bis(O,O-diethyl phosphorodithioate), 2-Chloro-1-(2,4-dichlorophenyl)-vinyl diethyl phosphate (chlorfenvinphos),
O,O-Dimethyl 0-(3-methyl-4-methylthiophenyl) phosphorothioate (fenthion),
Ethyl 3-methyl-4-(methylthio)phenyl(1-methylethyl) phosphoramidate (fenamiphos).

The carbamates include:
2-Isopropoxyphenyl methylcarbamate (propoxur),
1-Naphthyl N-methylcarbamate (carbaryl) or carbofuran.

The synthetic pyrethroids include compounds of the formula B

[chemical structure: Formula B - cyclopropane with R1, R2 substituted vinyl group, COO-CH(R3)-phenyl-O-phenyl with R4 and R5]

in which
R$^1$ and R$^2$ each represent halogen, optionally halogen-substituted alkyl, optionally halogen-substituted phenyl,
R$^3$ represents hydrogen or CN,
R$^4$ represents hydrogen or halogen,
R$^5$ represents hydrogen or halogen.

Preference is given to synthetic pyrethroids of the formula B in which
R$^1$ represents halogen, in particular fluorine, chlorine, bromine,
R$^2$ represents halogen, in particular fluorine, chlorine, bromine, trihalogenomethyl, phenyl, chlorophenyl,
R$^3$ represents hydrogen or CN,
R$^4$ represents hydrogen or fluorine,
R$^5$ represents hydrogen.

Particular preference is given to synthetic pyrethroids of the formula B in which
R$^1$ represents chlorine,
R$^2$ represents chlorine, trifluoromethyl, p-chlorophenyl,
R$^3$ represents CN,
R$^4$ represents hydrogen or fluorine,
R$^5$ represents hydrogen.

In particular, compounds of the formula B may be mentioned in which
R$^1$ represents chlorine,
R$^2$ represents chlorine or p-chlorophenyl,
R$^3$ represents CN,
R$^4$ represents fluorine in 4-position,
R$^5$ represents hydrogen.

Specific examples are:
(α-Cyano-4-fluoro-3-phenoxy)benzyl 3-[2-(4-chlorophenyl)-2-chlorovinyl]-2,2-dimethyl-cyclopropanecarboxylate (flumethrin),
α-Cyano(4-fluoro-3-phenoxy)-benzyl 2,2-dimethyl-3-(2,2-dichlorovinyl)-cyclopropanecarboxylate (cyfluthrin) and its enantiomers and stereoisomers,
α-Cyano-3-phenoxybenzyl (±)-cis,trans-3-(2,2-dibromovinyl)-2,2-dimethylcyclopropanecarboxylate (deltamethrin),
α-Cyano-3-phenoxybenzyl 2,2-dimethyl-3-(2,2-dichlorovinyl)-cyclopropanecarboxylate (cypermethrin), 3-Phenoxybenzyl (±)-cis,trans-3-(2,2-dichlorovinyl)-2,2-dimethylcyclopropanecarboxylate (permethrin), α-Cyano-3-phenoxy-benzyl α-(p-Cl-phenyl)-isovalerate (fenvalerate), 2-Cyano-3-phenoxybenzyl-2-(2-chloro-α,α,α-trifluoro-p-toluidino)-3-methylbutyrate (fluvalinate).

The amidines include:

3-Methyl-2-[2,4-dimethyl-phenylimino]-thiazoline 2-(4-Chloro-2-methylphenylimino)-3-methylthiazolidine 2-(4-Chloro-2-methylphenylimino)-3-(isobutyl-1-enyl)-thiazolidine 1,5-Bis-(2,4-dimethylphenyl)-3-methyl-1,3,5-triazapenta-1,4-diene (amitraz).

The juvenile hormones and juvenile hormone-like substances include substituted diaryl ethers, benzoylureas and triazine derivatives.

The substituted diaryl ethers include, in particular, substituted alkoxydiphenyl ethers or alkoxydiphenylmethanes of the general formula C (C)

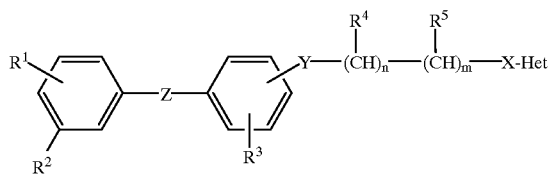

where $R^1$ represents hydrogen, halogen, alkyl, alkoxy, alkylthio, halogenoalkyl, halogenoalkoxy, halogenoalkylthio, dioxyalkylene, dioxyhalogenoalkylene, CN, $NO_2$, alkenyl, alkinyl, alkoxyalkyl, alkoxyalkoxy, hydroxyalkoxy, $R^2$ represents the radicals mentioned under $R^1$, $R^3$ represents the radicals mentioned under $R^1$, $R^4$ represents hydrogen, alkyl, halogenoalkyl or halogen, $R^5$ represents the radicals mentioned under $R^4$, Het represents optionally substituted heteroaryl which is linked to the remaining radical, although not via the heteroatom, X, Y independently of one another each represent —O—, —S—, Z represents —O—, —S—, —$CH_2$—, —$CHCH_3$—, —$C(CH_3)_2$—, m and n independently of one another each represent 0, 1, 2, 3.

Particular preference is given to compounds of the formula C in which $R^1$ represents hydrogen, methyl, trifluoromethyl, methoxy, trifluoromethoxy, chlorine, fluorine, $R^2$ represents hydrogen, $R^3$ represents hydrogen, fluorine, chlorine, methyl, $R^4$ represents hydrogen or methyl, $R^5$ represents methyl, ethyl, trifluoromethyl or hydrogen, Het represents pyridyl or pyridazinyl, each of which is optionally substituted by fluorine, chlorine, methyl, $NO_2$, methoxy, methylmercapto, X represents O, Y represents O, Z represents O, $CH_2$ or —$C(CH_3)_2$—, m represents 1, n represents 1.

Specifically, the following compounds may be mentioned:

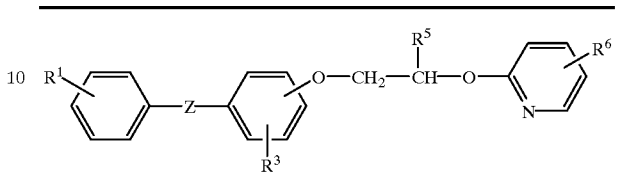

| $R^1$ | $R^3$ | $R^5$ | $R^6$ | Z |
|---|---|---|---|---|
| H | H | $CH_3$ | H | O |
| H | H | $CH_3$ | 2-Cl | O |
| 5-F | H | $CH_3$ | H | O |
| H | H | $CF_3$ | H | O |
| H | H | $C_2H_5$ | H | O |
| H | H | H | H | O |
| H | H | $CH_3$ | H | $CH_2$ |
| H | H | $CH_3$ | H | $C(CH_3)_2$ |

The benzoylureas include compounds of the formula (D):

(D)

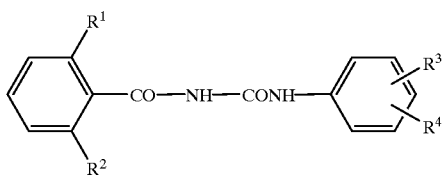

where $R^1$ represents halogen, $R^2$ represents hydrogen or halogen, $R^3$ represents hydrogen, halogen or $C_{1-4}$-alkyl, $R^4$ represents halogen, 1–5-halogeno-$C_{1-4}$-alkyl, $C_{1-4}$-alkoxy, 1–5-halogeno-$C_{1-4}$-alkoxy, $C_{1-4}$-alkylthio, 1–5-halogeno-$C_{1-4}$-alkylthio, phenoxy or pyridyloxy which may optionally be substituted by halogen, $C_{1-4}$-alkyl, 1–5-halogeno-$C_{1-4}$-alkyl, $C_{1-4}$-alkoxy, 1–5-halogeno-$C_{1-4}$-alkoxy, $C_{1-4}$-alkylthio, 1–5-halogeno-$C_{1-4}$-alkylthio.

Particular mention may be made of:

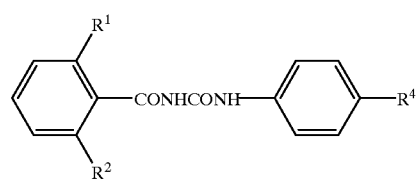

| $R^1$ | $R^2$ | $R^4$ |
|---|---|---|
| H | Cl | $CF_3$ |
| Cl | Cl | $CF_3$ |
| F | F | $CF_3$ |
| H | F | $CF_3$ |
| H | Cl | $SCF_3$ |
| F | F | $SCF_3$ |
| H | F | $SCF_3$ |

-continued

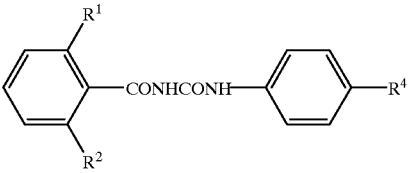

| R$^1$ | R$^2$ | R$^4$ |
|---|---|---|
| H | Cl | OCF$_3$ |
| F | F | OCF$_3$ |
| H | F | OCF$_3$ |
| F | F | O—⟨C$_6$H$_4$⟩—Cl |
| F | F | O—⟨C$_6$H$_4$⟩—CF$_3$ |
| F | F | O—⟨C$_6$H$_4$⟩—CF$_3$ |

The triazines include compounds of the formula (E)

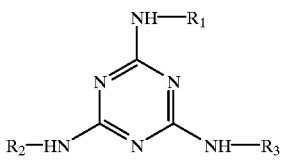

(E)

in which

R$_1$ represents cyclopropyl or isopropyl,

R$_2$ represents hydrogen, halogen, C$_1$–C$_{12}$-alkylcarbonyl, cyclopropylcarbonyl, C$_1$–C$_{12}$-alkylcarbamoyl, C$_1$–C$_{12}$-alkylthiocarbamoyl or C$_2$–C$_6$-alkenylcarbamoyl; and R$_3$ represents hydrogen, C$_1$–C$_{12}$-alkyl, cyclopropyl, C$_2$–C$_6$-alkenyl, C$_1$–C$_{12}$-alkylcarbonyl, cyclopropylcarbonyl, C$_1$–C$_{12}$-alkylcarbamoyl, C$_1$–C$_{12}$-alkylthiocarbamoyl or C$_2$–C$_6$-alkenylcarbamoyl and acid addition salts thereof which are nontoxic for warm-blooded animals.

In particular, mention may be made of:

| R$_1$ | R$_2$ | R$_3$ |
|---|---|---|
| cyclopropyl | H | H |
| cyclopropyl | H | CH$_3$ |
| cyclopropyl | H | C$_2$H$_5$ |
| cyclopropyl | H | C$_3$H$_7$-n |
| cyclopropyl | H | C$_4$H$_9$-n |
| cyclopropyl | H | C$_5$H$_{11}$-n |
| cyclopropyl | H | C$_6$H$_{13}$-n |
| cyclopropyl | H | C$_7$H$_{15}$-n |
| cyclopropyl | H | C$_8$H$_{17}$-n |
| cyclopropyl | H | C$_{12}$H$_{25}$-n |
| cyclopropyl | H | CH$_2$-C$_4$H$_9$-t |
| cyclopropyl | H | CH$_2$CH(CH$_3$)C$_2$H$_5$ |
| cyclopropyl | H | CH$_2$CH=CH$_2$ |
| cyclopropyl | Cl | C$_2$H$_5$ |
| cyclopropyl | Cl | C$_6$H$_{13}$-n |
| cyclopropyl | Cl | C$_8$H$_{17}$-n |
| cyclopropyl | Cl | C$_{12}$H$_{25}$-n |
| cyclopropyl | H | cyclopropyl |
| cyclopropyl | H | COCH$_3$ |
| cyclopropyl | H | COCH$_3$ HCl |
| cyclopropyl | H | COC$_2$H$_5$ HCl |
| cyclopropyl | H | COC$_2$H$_5$ |
| cyclopropyl | H | COC$_3$H$_7$-n |
| cyclopropyl | H | COC$_3$H$_7$-i |
| cyclopropyl | H | COC$_4$H$_9$-t HCl |
| cyclopropyl | H | COC$_4$H$_9$-n |
| cyclopropyl | H | COC$_6$H$_{13}$-n |
| cyclopropyl | H | COC$_{11}$H$_{23}$-n |
| cyclopropyl | COCH$_3$ | COC$_2$H$_5$ |
| cyclopropyl | COC$_3$H$_7$-n | COC$_6$H$_{13}$-n |
| cyclopropyl | COCH$_3$ | COC$_3$H$_7$-n |
| cyclopropyl | COC$_2$H$_5$ | COC$_3$H$_7$-n |
| cyclopropyl | H | COcyclopropyl |
| cyclopropyl | COcyclopropyl | COcyclopropyl |
| cyclopropyl | COCH$_3$ | COCH$_3$ |
| isopropyl | H | H |
| isopropyl | H | COCH$_3$ |
| isopropyl | H | COC$_3$H$_7$-n |
| cyclopropyl | H | CONHCH$_3$ |
| cyclopropyl | H | CONHC$_3$H$_7$-i |
| cyclopropyl | CONHCH$_3$ | CONHCH$_3$ |
| cyclopropyl | H | CSNHCH$_3$ |
| cyclopropyl | H | CONHCH$_2$CH=CH$_2$ |
| cyclopropyl | CONHCH$_2$CH=CH$_2$ | CONHCH$_2$CH=CH$_2$ |
| cyclopropyl | CSNHCH$_3$ | CSNHCH$_3$ |

The compositions according to the invention may optionally contain further insecticides and optionally additionally one or more microbicides.

Preference is given to the insecticides and fungicides mentioned in WO 94/29 268. The compounds mentioned in this document are expressly incorporated into the present application by way of reference.

Very particular emphasis should be given to the insecticides chlorpyriphos, phoxim, silafluofin, alphamethrin, cyfluthrin, cypermethrin, deltamethrin, isofenphos, fenamiphos, permethrin, imidacloprid, NI-25, flufenoxuron, hexaflumuron and triflumuron, and the fungicides epoxyconazole, fenaminosulf, sodium [4-(dimethylamino) phenyl]diazenesulfonate, hexaconazole, azaconazole, propiconazole, tebuconazole, cyproconazole, metconazole, imazalil, dichlorfluanid, tolylfluanid, 3-iodo-2-propinyl-butylcarbamate, N-octyl-isothiazolin-3-one and 4,5-dichloro-N-octyl-isothiazolin-3-one.

The compositions according to the invention exhibit good insecticidal activity against insects which destroy industrial materials.

By way of example and by way of preference, but without imposing any limitations, the following insects may be mentioned:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec. *Dinoderus minutus.*

Hymenopterans, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina*.

In the present context, industrial materials are to be understood as meaning non-living materials, such as, preferably, plastics, adhesives, glues, papers and cardboards, leather, wood and timber products and paints.

The material to be protected against infestation by insects is very particularly preferably wood and timber products, and also wood-containing buildings or parts of buildings.

Wood and timber products which can be protected by the composition according to the invention or by mixtures comprising this composition are, for example:

construction timber, wooden beams, railway sleepers, bridge components, jetties, wooden vehicles, boxes, pallets, containers, telephone poles, wood cladding, wooden windows and doors, plywood, particleboard, joinery articles, or wood products which, quite generally, are used in the construction of houses or boats or in joinery.

Carrier materials used for the compositions according to the invention are natural organic compounds or synthetic organic compounds. Examples thereof which may be mentioned are porous organic carriers, such as sawdust, wood slivers or shavings, ground or chipped tree bark or tree bark slivers or shavings, peat, lignin, coconut fiber and coconut meal and sugar beet pulp residues.

The particle size of the carrier material is 10 mm maximum. The compositions according to the invention are then applied dry or packaged in biodegradable or water-soluble films or paper.

The carrier material preferably has a particle size of up to 0.2 mm. The compositions according to the invention are then applied dry or packaged in biodegradable films or paper. However, they can also be suspended in water or applied to the soil, for example along or under base walls, foundations and stone or concrete ceilings of buildings, using foaming agents and appropriate sprayers or pumps. Compositions with a particle size of 0.2 to 10 mm can be scattered onto the soil or incorporated into the soil, or in the case of fiberous material, applied as mats or imbeded in sheets of water soluble and/or biodegradable plastic.

The compositions or concentrates according to the invention comprise active compound in a concentration of 0.0001 to 95% by weight, in particular 0.001 to 60% by weight.

The amount of the compositions employed depends on the species and the occurrence of the insects and the medium. The optimum application rate can be determined upon use in each case by test series. In general, however, it is sufficient to employ 0.0001 to 20% by weight, preferably 0.001 to 10% by weight, of the active compound, based on the material to be protected.

The compositions according to the invention may contain formulation auxiliaries. Formulation auxiliaries which may be mentioned are solvents and/or diluents, emulsifiers or wetting agents, binders, fixing agents or plasticizers.

The solvents and/or diluents used are organochemical solvents or solvent mixtures and/or oily or oil-type organochemical solvents or solvent mixtures of low volatility and/or polar organochemical solvents or solvent mixtures and/or water and, if appropriate, emulsifiers and/or wetting agents.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are appropriate mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents having hydroxyl and/or ester and/or ether groups, such as, for example, glycol ethers, esters and the like.

The organochemical binders used are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odor-masking substances and inhibitors or anti-corrosives known per se and the like can also be employed.

The composition or the concentrate preferably comprises at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the above-mentioned binder can be replaced by a fixative (mixture) or a plasticizer (mixture). These additives are intended to prevent volatilization of the active compounds and crystallization or precipitation. They preferably replace 0.01 to 30% of the binder (based on 100% of the binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulfonic esters.

Fixatives are chemically based on polyvinyl alkyl ethers, such as, for example, polyvinyl methyl ether, or ketones, such as benzophenone or ethylene benzophenone.

A particularly useful solvent/diluent is water, if appropriate as a mixture with one or more of the abovementioned organochemical solvents/diluents, emulsifiers and dispersants.

The compositions according to the invention are prepared, for example, by mixing the active compounds together as powders or by dissolving them in suitable solvents, adding formulation auxiliaries and admixing the carrier substances. The components may be added in any order.

The water-soluble polymer films mentioned for use as packaging are known. They are films made of polyvinyl alcohol polymers, for example ethylenephenyl alcohol.

The compositions are packaged in the form of tubes which may optionally be segmented. The diameter of the tubes is from 1 to 20 cm, preferably 2 to 10 cm. The length of the segments is from 5 to 30 cm, preferably 10 to 20 cm.

The compositions may also be packaged, for example, in bags.

In the case of adsorption onto or into coconut fibers, application may be carried out as a rope, as woven mats or in the form of loose fibers or as a powder.

What is claimed is:

1. A method for delaying the microbial soil degradation of imidacloprid, said method comprising:

(1) mixing said imidacloprid with:

(a) one or more carrier materials having a particle size of up to 10 mm, said one or more carrier materials additionally being organic natural compounds and organic synthetic compounds selected from the group consisting of sawdust, wood slivers, wood shavings, ground tree bark, chipped tree bark slivers, tree bark shavings, peat, lignin, coconut fiber, coconut meal and sugar beet pulp residues;

(b) optionally, one or more microbiocidally active compounds;

(c) optionally, one or more attractants or development-inhibitory compounds; and (d) optionally, one or more formulation auxilliaries; and (2) applying the mixture to the soil.

2. A method of protecting buildings and materials against insects, said method comprising applying to the soil an effective amount of a composition against insects comprising:

(a) imidacloprid;

(b) one or more carrier materials having a particle size of up to 10 mm, said one or more carrier materials additionally being organic natural compounds and organic synthetic compounds selected from the group consisting of sawdust, wood slivers, wood shavings, ground tree bark, chipped tree bark slivers, tree bark shavings, peat, lignin, coconut fiber, coconut meal and sugar beet pulp residues;

(c) optionally, one or more microbiocidally active compounds;

(d) optionally, one or more attractants or development-inhibitory compounds; and (e) optionally, one or more formulation auxilliaries.

3. The method of claim 2 wherein said insects are termites.

* * * * *